United States Patent
Son et al.

(10) Patent No.: US 12,276,650 B2
(45) Date of Patent: *Apr. 15, 2025

(54) METHOD AND DEVICE FOR CALCULATING CONCENTRATION OF HYDROCARBON IN FUEL EVAPORATION GAS OF VEHICLE

(71) Applicants: Hyundai Motor Company, Seoul (KR); Kia Corporation, Seoul (KR)

(72) Inventors: Jung Seop Son, Seoul (KR); Taegon Noh, Seoul (KR); HyungSeok Yoon, Hwaseong-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 203 days.

This patent is subject to a terminal disclaimer.

(21) Appl. No.: 17/993,781

(22) Filed: Nov. 23, 2022

(65) Prior Publication Data

US 2023/0408480 A1    Dec. 21, 2023

(30) Foreign Application Priority Data

Jun. 15, 2022   (KR) .................. 10-2022-0072690

(51) Int. Cl.
*G01N 33/22* (2006.01)
*F02D 41/00* (2006.01)
(Continued)

(52) U.S. Cl.
CPC ......... *G01N 33/225* (2013.01); *F02D 41/004* (2013.01); *F02D 41/0045* (2013.01);
(Continued)

(58) Field of Classification Search
CPC ...... G01N 33/225; G01N 9/26; F02D 41/004; F02D 41/0045; F02D 2041/1432;
(Continued)

(56) References Cited

U.S. PATENT DOCUMENTS

| | | | |
|---|---|---|---|
| 7,234,450 B1 * | 6/2007 | Takakura | F02D 41/0045 73/114.38 |
| 11,754,006 B1 * | 9/2023 | Son | F02M 25/0827 123/520 |

(Continued)

*Primary Examiner* — Phutthiwat Wongwian
*Assistant Examiner* — Susan E Scharpf
(74) *Attorney, Agent, or Firm* — Fish & Richardson P.C.

(57) ABSTRACT

A method includes calculating a first fuel evaporation gas density in a purge pump of a vehicle based on a pressure difference between a front end and a rear end of the purge pump, a radius of a fluid passage of the purge pump, a number of rotations of the purge pump, and an opening amount of a purge control solenoid valve, filtering the first fuel evaporation gas density, calculating a second fuel evaporation gas density in the purge pump based on the filtered first fuel evaporation gas density, calculating a third fuel evaporation gas density in a standard temperature and pressure state based on the second fuel evaporation gas density, a current pressure in the purge pump, and a current temperature in the purge pump, and calculating a concentration of hydrocarbon in a fuel evaporation gas in the purge pump based on the third fuel evaporation gas density.

10 Claims, 2 Drawing Sheets

(51) Int. Cl.
   *F02D 41/14* (2006.01)
   *F02M 25/08* (2006.01)
   *G01N 9/26* (2006.01)

(52) U.S. Cl.
   CPC ........ *F02M 25/08* (2013.01); *F02M 25/0836* (2013.01); *F02M 25/089* (2013.01); *G01N 9/26* (2013.01); *F02D 2041/1432* (2013.01); *F02M 2025/0845* (2013.01)

(58) Field of Classification Search
   CPC .. F02M 25/08; F02M 25/0836; F02M 25/089; F02M 2025/0845
   See application file for complete search history.

(56) References Cited

U.S. PATENT DOCUMENTS

| | | | |
|---|---|---|---|
| 2017/0152802 A1* | 6/2017 | Casetti | F02D 41/0007 |
| 2017/0342917 A1* | 11/2017 | Dekar | F02M 25/08 |
| 2018/0142631 A1* | 5/2018 | Sager | F02D 41/0007 |
| 2019/0101082 A1* | 4/2019 | Sanuma | F02M 25/089 |
| 2019/0186393 A1* | 6/2019 | Oh | F02M 35/10222 |
| 2020/0191085 A1* | 6/2020 | Oh | F02D 13/0226 |
| 2021/0071598 A1* | 3/2021 | Nakagawa | F02D 41/003 |
| 2021/0270215 A1* | 9/2021 | Nakagawa | B01D 53/0454 |
| 2023/0408480 A1* | 12/2023 | Son | F02D 41/0045 |

* cited by examiner

METHOD AND DEVICE FOR CALCULATING CONCENTRATION OF HYDROCARBON IN FUEL EVAPORATION GAS OF VEHICLE

CROSS-REFERENCE TO RELATED APPLICATION

This application claims priority to and the benefit of Korean Patent Application No. 10-2022-0072690 filed in the Korean Intellectual Property Office on Jun. 15, 2022, the entire contents of which are incorporated herein by reference.

TECHNICAL FIELD

The present disclosure relates to a vehicle, and more particularly, to a method and a device for calculating concentration of hydrocarbon in fuel evaporation gas of a vehicle.

BACKGROUND

Fuel stored in a fuel tank of a vehicle evaporates according to a flow in the fuel tank and an internal temperature of the fuel tank to generate fuel evaporation gas. When the fuel evaporation gas is leaked into the atmosphere, it causes environmental pollution. To prevent the environmental pollution, a purge system collects the fuel evaporation gas in a canister and then introduces the fuel evaporation gas into an intake system of an engine to combust the fuel evaporation gas.

The purge system supplies the fuel evaporation gas to the intake system using a pressure acting on the fuel evaporation gas according to a negative pressure formed in the intake system. However, it is difficult for a turbocharger mounted engine or a hybrid vehicle to generate negative pressure at a front end of an engine intake valve so that it is difficult to apply the purge system using negative intake pressure to the turbocharger mounted engine or the hybrid vehicle.

An active purge system operates a purge pump to forcibly purge the fuel evaporation gas to solve the problem.

The above information disclosed in this Background section is only for enhancement of understanding of the background of the disclosure, and therefore it may contain information that does not form the prior art that is already known in this country to a person of ordinary skill in the art.

SUMMARY

The present disclosure has been made in an effort to provide a method and a device for calculating concentration of hydrocarbon in fuel evaporation gas of a vehicle which are capable of accurately calculating the concentration of hydrocarbon (HC) that is a fuel component in the fuel evaporation gas of the vehicle.

According to one aspect of the subject matter described in this application, a method for calculating the concentration of hydrocarbon in the fuel evaporation gas of the vehicle includes: calculating, by a controller, a first fuel evaporation gas density in a purge pump included in an active fuel vapor purge system of the vehicle based on a difference between a pressure signal at a front end of the purge pump and a pressure signal at a rear end of the purge pump, a radius of a fluid passage of the purge pump, a number of rotations signal of the purge pump, and an opening amount signal of a purge control solenoid valve that supplies fuel evaporation gas pumped by the purge pump to an intake manifold of an engine of the vehicle; filtering, by the controller, the first fuel evaporation gas density using a filter for controlling an amount of change in the first fuel evaporation gas density when the amount of change in the first fuel evaporation gas density is greater than or equal to a reference change amount; calculating, by the controller, a second fuel evaporation gas density in the purge pump based on the filtered first fuel evaporation gas density; calculating, by the controller, a third fuel evaporation gas density in a standard temperature and pressure state based on the second fuel evaporation gas density, a current pressure in the purge pump, and a current temperature in the purge pump; and calculating, by the controller, a concentration of hydrocarbon within a fuel evaporation gas in the purge pump based on the third fuel evaporation gas density.

The controller may be configured to use a low pass filter having a time constant greater than a reference time constant to filter the first fuel evaporation gas density.

The hydrocarbon may include butane.

According to another aspect, a device for calculating the concentration of hydrocarbon in the fuel evaporation gas of the vehicle includes: a data detector that includes a pressure sensor detecting a pressure signal of a front end of a purge pump and a pressure signal of a rear end of the purge pump that is included in an active fuel vapor purge system of the vehicle, a number of rotations sensor detecting a number of rotations signal of the purge pump, and an opening amount sensor detecting an opening amount signal of a purge control solenoid valve that supplies fuel evaporation gas pumped by the purge pump to an intake manifold of an engine of the vehicle; and a controller configured to calculate a first fuel evaporation gas density in the purge pump based on a difference between the pressure signal at the front end of the purge pump and the pressure signal at the rear end of the purge pump, a radius of a fluid passage of the purge pump, the number of rotations signal of the purge pump, and the opening amount signal of the purge control solenoid valve. The controller may be configured to filter the first fuel evaporation gas density using a filter for controlling an amount of change in the first fuel evaporation gas density when the amount of change in the first fuel evaporation gas density is greater than or equal to a reference change amount. The controller may be configured to calculate a second fuel evaporation gas density in the purge pump based on the filtered first fuel evaporation gas density. The controller may be configured to calculate a third fuel evaporation gas density in a standard temperature and pressure state based on the second fuel evaporation gas density, a current pressure in the purge pump, and a current temperature in the purge pump. The controller may be configured to calculate a concentration of hydrocarbon within a fuel evaporation gas in the purge pump based on the third fuel evaporation gas density.

The controller may be configured to use a low pass filter having a time constant greater than a reference time constant to filter the first fuel evaporation gas density.

The hydrocarbon may include butane.

The method and the device for calculating the concentration of hydrocarbon in the fuel evaporation gas of the vehicle may accurately calculate the concentration of hydrocarbon that is the fuel component fuel evaporation gas of the vehicle.

BRIEF DESCRIPTION OF THE DRAWINGS

A brief description of the drawings will be provided to more sufficiently understand the drawings which are used in the detailed description of the present disclosure.

DETAILED DESCRIPTION

Figure 1:
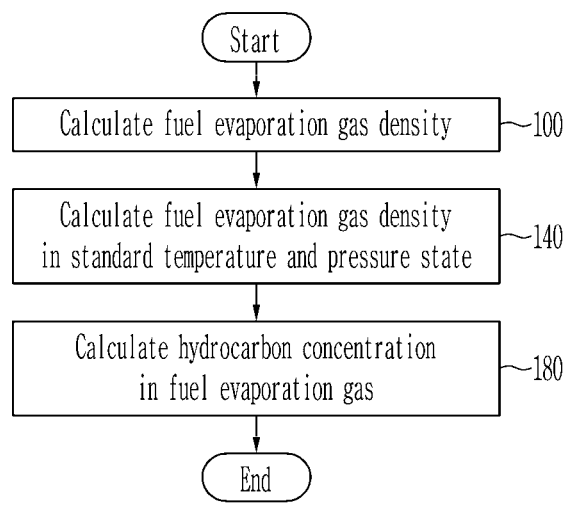
FIG. 1 is a flowchart illustrating an example of a method for calculating concentration of hydrocarbon in fuel evaporation gas of a vehicle.

In order to sufficiently understand the present disclosure and the object achieved by embodying the present disclosure, the accompanying drawings illustrating implementations of the present disclosure and contents described in the accompanying drawings are to be referenced.

Hereinafter, the present disclosure will be described in detail by describing implementations of the present disclosure with reference to the accompanying drawings. In describing the present disclosure, well-known configurations or functions will not be described in detail since they may unnecessarily obscure the gist of the present disclosure. Throughout the accompanying drawings, the same reference numerals will be used to denote the same components.

Terms used in the present specification are only used in order to describe specific implementations rather than limiting the present disclosure. Singular forms are to include plural forms unless the context clearly indicates otherwise. It will be further understood that the terms "include" or "have" used in the present specification specify the presence of features, numerals, steps, operations, components, or parts mentioned in the present specification, or a combination thereof, but do not preclude the presence or addition of one or more other features, numerals, steps, operations, components, parts, or a combination thereof.

Throughout this specification and the claims that follow, when it is described that an element is "coupled" to another element, the element may be "directly coupled" to the other element or "electrically or mechanically coupled" to the other element through a third element.

Unless defined otherwise, it is to be understood that the terms used in the present specification including technical and scientific terms have the same meanings as those that are generally understood by those skilled in the art. The terms defined by the dictionary are identical with the meanings within the context of the related art, and they should not be ideally or excessively formally defined unless the context clearly dictates otherwise.

An active purge system that is a related art may not accurately calculate concentration of hydrocarbon (HC) in fuel evaporation gas when the concentration of fuel evaporation gas introduced into a purge pump sharply increases or decreases.

Figure 2:
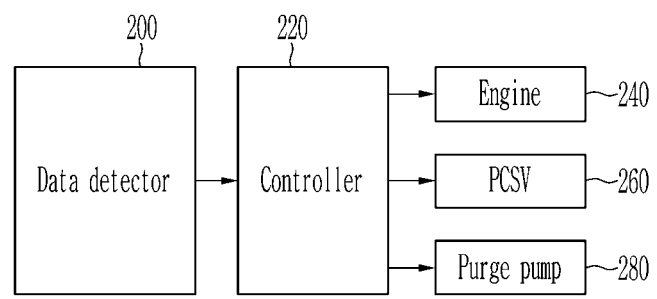
FIG. 2 is a block diagram illustrating an example of a device for calculating concentration of hydrocarbon in fuel evaporation gas of a vehicle to which the method for calculating the concentration of hydrocarbon in the fuel evaporation gas of the vehicle shown in FIG. 1 is applied.

FIG. 1 is a flowchart illustrating an example of a method for calculating concentration of hydrocarbon in fuel evaporation gas of a vehicle. FIG. 2 is a block diagram illustrating an example of a device for calculating concentration of hydrocarbon in fuel evaporation gas of a vehicle to which the method for calculating the concentration of hydrocarbon in the fuel evaporation gas of the vehicle shown in FIG. 1 is applied.

In some implementations, referring to FIG. 1 and FIG. 2, in a step 100, a controller 220 may calculate a first fuel evaporation gas density in a purge pump 280 (or a first density of fuel evaporation gas introduced through the purge pump) based on a difference between a pressure signal at a front end of the purge pump and a pressure signal at a rear end of the purge pump included in an active fuel vapor purge system (or an active fuel evaporation gas purge system) of the vehicle (e.g., a hybrid electric vehicle), a radius of a fluid passage of the purge pump (or a radius of an impeller of the purge pump), a number of rotations signal of the purge pump, and an opening amount signal of a purge control solenoid valve (PCSV) 260 that supplies fuel evaporation gas pumped (supplied) by the purge pump to an intake manifold of an engine 240. The fuel evaporation gas may mean a gas (a fuel vapor) evaporated from a fuel tank of the vehicle. For example, the controller 220 may calculate the first fuel evaporation gas density in the purge pump 280 using the following equation.

$$\text{First fuel evaporation gas density} = (2 \times \Delta P) / \{K \times (2\pi \cdot r \cdot f)^2\}$$

In the equation, the $\Delta P$ may be a pressure difference between both ends of the purge pump 280, the K may be a flow coefficient and may be determined according to an opening amount of the purge control solenoid valve (PCSV) 260 and a number of rotations of the purge pump 280, the r may be the radius of the fluid passage of the purge pump 280, and the f may be a number of rotations of the purge pump 280 and a unit of the f may be Hz.

As shown in FIG. 2, the vehicle may include a data detector 200, the controller 220, the engine 240, the purge control solenoid valve (PCSV) 260, and the purge pump 280 including a motor and the impeller rotating by power of the motor.

The active fuel vapor purge system may include the purge control solenoid valve (PCSV) 260 and the purge pump 280, and may forcibly purge the fuel evaporation gas of the vehicle by operating the purge pump.

The purge pump 280 may pump the fuel evaporation gas collected from a canister to the purge control solenoid valve (PCSV) 260. For example, the purge pump 280 may be operated when an amount of hydrocarbon in the fuel evaporation gas is greater than a set amount. The canister may collect the fuel evaporation gas that evaporates from the fuel tank of the vehicle. The purge control solenoid valve (PCSV) 260 may selectively block the fuel evaporation gas collected from the canister and may supply the pumped fuel evaporation gas to the intake manifold of the engine 240.

The device for calculating the concentration of hydrocarbon in the fuel evaporation gas of the vehicle may include the data detector 200 and the controller 220.

The data detector 200 may include a pressure sensor, a number of rotations sensor, and an opening amount sensor. The pressure sensor may detect the pressure signal of the front end of the purge pump 280 and the pressure signal of the rear end of the purge pump and may provide (or transmit) the detected signals to the controller 220. The number of rotations sensor may detect the number of rotations signal of the purge pump 280 to provide the detected signal to the controller 220. The opening amount sensor may detect the opening amount signal of the PCSV 260 to provide the detected signal to the controller 220.

The controller 220 may be an electronic control unit (ECU) and may control an entire operation of the vehicle. For example, the controller 220 may be one or more microprocessors operated by a program (i.e., a control logic) or hardware (e.g., a microcomputer) including the microprocessor. The program may include a series of commands for executing the method for calculating the concentration of hydrocarbon in the fuel evaporation gas of the vehicle. The commands may be stored in a memory of the controller 220.

The controller 220 may determine whether a fuel evaporation gas density in the purge pump 280 is increased or decreased using the calculated first fuel evaporation gas density. When the first fuel evaporation gas density increases or decreases rapidly (or when an amount of change in the first fuel evaporation gas density is greater than or equal to a reference change amount), the controller 220 may filter the first fuel evaporation gas density (e.g., the first fuel evaporation gas density value or the first fuel evaporation gas density signal) using a low pass filter (LPF) for controlling (adjusting) the amount of change in the first fuel evaporation gas density. For example, the amount of change may be a sharp change amount greater than the reference change amount. The reference change amount may be determined by a test (or experiment).

When the amount of change in the first fuel evaporation gas density is greater than or equal to the reference change amount (or when the first fuel evaporation gas density changes rapidly), the controller 220 may use the low pass filter (LPF) having a time constant greater than a reference time constant to filter the first fuel evaporation gas density.

The controller 220 may calculate a second fuel evaporation gas density in the purge pump 280 based on the filtered first fuel evaporation gas density. Therefore, a more accurate fuel evaporation gas density in the purge pump 280 may be calculated. For example, the controller 220 may calculate the second fuel evaporation gas density using the equation for calculating the first fuel evaporation gas density.

According to a step 140 shown in FIG. 1, the controller 220 may calculate a third fuel evaporation gas density in a standard temperature and pressure state based on the second fuel evaporation gas density, a current pressure in the purge pump 280, and a current temperature in the purge pump. For example, the controller 220 may calculate the third fuel evaporation gas density in a standard temperature and pressure state using the following equation.

Third fuel evaporation gas density in the standard temperature and pressure state=the second fuel evaporation gas density×(1/(the current pressure))×{(273.15+(the current temperature))/273.15}

In the equation, the current pressure and the current temperature may be the current pressure and the current temperature in the purge pump 280, and may be detected by a sensor included in the data detector 200 to be provided to the controller 220.

According to a step 180, the controller 220 may calculate a concentration of hydrocarbon within a fuel evaporation gas in the purge pump 280 using the third fuel evaporation gas density in the standard temperature and pressure state. For example, the controller 220 may calculate the concentration of hydrocarbon in the fuel evaporation gas using the equation below. For example, the hydrocarbon may be butane.

Concentration of hydrocarbon in the fuel evaporation gas={(the third fuel evaporation gas density in the standard temperature and pressure state−an air density in the standard temperature and pressure state)/(a density of hydrocarbon in the standard temperature and pressure state−the air density in the standard temperature and pressure state)}×100

For example, the controller 220 may calculate a concentration of the butane in the fuel evaporation gas by designating the hydrocarbon in the equation as the butane. A unit of the concentration of the hydrocarbon may be %.

The controller 220 may control the engine 240, the PCSV 260, and the purge pump 280 based on the calculated hydrocarbon concentration in the fuel evaporation gas. For example, the controller 220 may control an injector of the engine 240 based on the calculated hydrocarbon concentration in the fuel evaporation gas so that the controller adjusts an amount of fuel that is used to control an air-fuel ratio of the engine and is supplied to the engine.

The components, "~units", "~or", blocks, or modules used in the present disclosure may be implemented by software such as tasks, classes, sub-routines, processes, objects, execution threads, or programs performed in a predetermined region on a memory or hardware such as a field-programmable gate array (FPGA) or an application-specific integrated circuit (ASIC) and may be implemented by a combination of the software and the hardware. The components, '~part', or the like may be embedded in a computer-readable storage medium, and some part thereof may be dispersedly distributed in a plurality of computers.

As set forth above, implementations have been disclosed in the accompanying drawings and the specification. Herein, specific terms have been used, but are just used for the purpose of describing the present disclosure and are not used for qualifying the meaning or limiting the scope of the present disclosure, which is disclosed in the appended claims. Therefore, it will be understood by those skilled in the art that various modifications and equivalent implementations are possible from the present disclosure. Accordingly, the actual technical protection scope of the present disclosure is determined by the spirit of the appended claims.

What is claimed is:

1. A method for providing fuel to an engine of a vehicle based on calculating a concentration of hydrocarbon in fuel evaporation gas of the vehicle, the vehicle further including an active fuel vapor purge system that includes a purge pump and a purge control solenoid valve configured to supply fuel evaporation gas pumped by the purge pump to an intake manifold of the engine, the method comprising:

calculating, by a controller, a first fuel evaporation gas density in the purge pump based on (i) a difference between a first pressure detected at a front end of the purge pump and a second pressure detected at a rear end of the purge pump, (ii) a radius of a fluid passage of the purge pump, (iii) a number of rotations of the purge pump, and (iv) an opening amount of the purge control solenoid valve;

filtering, by the controller, the first fuel evaporation gas density using a signal filter, the signal filter being configured to control an amount of change in the first fuel evaporation gas density based on the amount of change in the first fuel evaporation gas density being greater than or equal to a reference change amount;

calculating, by the controller, a second fuel evaporation gas density in the purge pump based on the filtered first fuel evaporation gas density;

calculating, by the controller, a third fuel evaporation gas density in a standard temperature and a standard pressure state based on the second fuel evaporation gas density, a current pressure in the purge pump, and a current temperature in the purge pump;

calculating, by the controller, the concentration of hydrocarbon in the fuel evaporation gas in the purge pump based on the third fuel evaporation gas density; and controlling, by the controller, at least one of the engine, the purge control solenoid valve, or the purge pump based on the concentration of hydrocarbon to thereby adjust an amount of the fuel provided to the engine and control an air-fuel ratio for operation of the engine.

2. The method of claim 1, wherein filtering the first fuel evaporation gas density is performed using a low pass filter, the low pass filter having a time constant that is greater than a reference time constant.

3. The method of claim 1, wherein the hydrocarbon in the fuel evaporation gas in the purge pump includes butane.

4. The method of claim 1, wherein the first fuel evaporation gas density is equal to $(2 \times \Delta P)/\{K \times (2\pi \cdot r \cdot f)2\}$, where
- $\Delta P$ denotes the difference between the first pressure detected at the front end of the purge pump and the second pressure detected at the rear end of the purge pump,
- r denotes the radius of the fluid passage of the purge pump,
- f denotes a frequency corresponding to the number of rotations of the purge pump, and
- K denotes a flow coefficient corresponding to the opening amount of the purge control solenoid valve.

5. The method of claim 1, wherein the third fuel evaporation gas density is equal to the second fuel evaporation gas density$\times$(1/(the current pressure))$\times$\{(273.15+(the current temperature))/273.15\}.

6. A device configured to provide fuel to an engine of a vehicle based on calculating a concentration of hydrocarbon in fuel evaporation gas of the vehicle, the vehicle further including an active fuel vapor purge system that includes a purge pump and a purge control solenoid valve configured to supply fuel evaporation gas pumped by the purge pump to an intake manifold of the engine, the device comprising:
- a data detector comprising:
  - a pressure sensor configured to detect a first pressure at a front end of the purge pump and a second pressure at a rear end of the purge pump,
  - a number of rotations sensor configured to detect a number of rotations of the purge pump, and
  - an opening amount sensor configured to detect an opening amount of the purge control solenoid valve; and
- a controller configured to communicate with the data detector, the controller being configured to:
  - calculate a first fuel evaporation gas density in the purge pump based on (i) a difference between the first pressure detected at the front end of the purge pump and the second pressure detected at the rear end of the purge pump, (ii) a radius of a fluid passage of the purge pump, (iii) the number of rotations of the purge pump, and (iv) the opening amount of the purge control solenoid valve,
  - filter the first fuel evaporation gas density using a signal filter, the signal filter being configured to control an amount of change in the first fuel evaporation gas density based on the amount of change in the first fuel evaporation gas density being greater than or equal to a reference change amount,
  - calculate a second fuel evaporation gas density in the purge pump based on the filtered first fuel evaporation gas density,
  - calculate a third fuel evaporation gas density in a standard temperature and a standard pressure state based on the second fuel evaporation gas density, a current pressure in the purge pump, and a current temperature in the purge pump,
  - calculate the concentration of hydrocarbon in the fuel evaporation gas in the purge pump based on the third fuel evaporation gas density, and
  - control at least one of the engine, the purge control solenoid valve, or the purge pump based on the concentration of hydrocarbon to thereby adjust an amount of the fuel provided to the engine and control an air-fuel ratio for operation of the engine.

7. The device of claim 6, wherein the signal filter comprises a low pass filter having a time constant that is greater than a reference time constant.

8. The device of claim 6, wherein the hydrocarbon in the fuel evaporation gas in the purge pump includes butane.

9. The device of claim 6, wherein the first fuel evaporation gas density is equal to $(2 \times \Delta P)/\{K \times (2\pi \cdot r \cdot f)2\}$, where
- $\Delta P$ denotes the difference between the first pressure detected at the front end of the purge pump and the second pressure detected at the rear end of the purge pump,
- r denotes the radius of the fluid passage of the purge pump,
- f denotes a frequency corresponding to the number of rotations of the purge pump, and
- K denotes a flow coefficient corresponding to the opening amount of the purge control solenoid valve.

10. The device of claim 6, wherein the third fuel evaporation gas density is equal to the second fuel evaporation gas density$\times$(1/(the current pressure))$\times$\{(273.15+(the current temperature))/273.15\}.

* * * * *